US009186505B2

(12) United States Patent
Katsnelson (10) Patent No.: US 9,186,505 B2
(45) Date of Patent: Nov. 17, 2015

(54) TRANSCRANIAL ELECTROSTIMULATION DEVICE AND METHOD

(71) Applicant: Novo HB, LLC, Doylestown, PA (US)

(72) Inventor: Yakov Katsnelson, Edgewater, NJ (US)

(73) Assignee: NOVO HB, LLC, Doylestown, PA (US)

( * ) Notice: Subject to any disclaimer, the term of this patent is extended or adjusted under 35 U.S.C. 154(b) by 0 days.

(21) Appl. No.: 14/548,946

(22) Filed: Nov. 20, 2014

(65) Prior Publication Data

US 2015/0238759 A1 Aug. 27, 2015

Related U.S. Application Data

(60) Provisional application No. 61/942,709, filed on Feb. 21, 2014.

(51) Int. Cl.
*A61N 1/34* (2006.01)
*A61N 1/36* (2006.01)

(52) U.S. Cl.
CPC .......... *A61N 1/36014* (2013.01); *A61N 1/3606* (2013.01); *A61N 1/36067* (2013.01); *A61N 1/36082* (2013.01); *A61N 1/36103* (2013.01)

(58) Field of Classification Search
CPC .......... A61N 1/36067; A61N 1/36082; A61N 1/36103; A61N 1/3606; A61N 1/36014
USPC ............................... 607/46, 66, 115
See application file for complete search history.

(56) References Cited

U.S. PATENT DOCUMENTS

| 3,835,833 | A | 9/1974 | Limoge |
|---|---|---|---|
| 5,540,736 | A | 7/1996 | Haimovich et al. |
| 6,505,079 | B1 | 1/2003 | Foster et al. |
| 6,591,138 | B1 | 7/2003 | Fischell et al. |
| 6,904,322 | B2 | 6/2005 | Katsnelson |
| 7,769,463 | B2 | 8/2010 | Katsnelson |
| 8,958,882 | B1 * | 2/2015 | Hagedorn ............. A61N 2/006 607/45 |
| 2007/0142874 | A1 * | 6/2007 | John ............................. 607/45 |
| 2008/0319492 | A1 | 12/2008 | Katsnelson |
| 2009/0177243 | A1 | 7/2009 | Lebedev et al. |
| 2009/0299435 | A1 * | 12/2009 | Gliner et al. ................ 607/45 |
| 2011/0093033 | A1 | 4/2011 | Nekhendzy |
| 2011/0152975 | A1 | 6/2011 | Colthurst |
| 2011/0160811 | A1 | 6/2011 | Walker |
| 2011/0224753 | A1 | 9/2011 | Palermo et al. |
| 2012/0022610 | A1 | 1/2012 | Blum et al. |
| 2012/0109251 | A1 | 5/2012 | Lebedev et al. |

FOREIGN PATENT DOCUMENTS

| AU | 714744 | 1/2000 |
|---|---|---|
| AU | 2003208147 | 1/2005 |
| CA | 2434583 | 1/2005 |
| EP | 0801957 | 10/1997 |
| EP | 1502623 | 2/2005 |
| EP | 1997527 | 12/2008 |
| WO | 2008156747 | 12/2008 |
| WO | 2010057998 | 5/2010 |
| WO | 2010120823 | 10/2010 |

OTHER PUBLICATIONS

PCT US2014/016005; International Search Report & Written Opinion; Apr. 2, 2015; (6 pgs).

* cited by examiner

*Primary Examiner* — Theodore Stigell
*Assistant Examiner* — Michael Carey
(74) *Attorney, Agent, or Firm* — Gearhart Law, LLC (57) ABSTRACT

Transcranial electrostimulation is used to treat a number of ailments including depression and pain management amongst others. However, long term transcranial electrostimulation can lead to the hyperpolarization in the membrane of the post synaptic neurons reducing or eliminating the positive effects. Thus, by using a "white noise" (clock) generator and taking advantage of polarity inversions empirical evidence has shown this to reduce or prevent the negative effects associated with long term use of current transcranial devices and methods.

19 Claims, 4 Drawing Sheets

TRANSCRANIAL ELECTROSTIMULATION DEVICE AND METHOD

CLAIM OF PRIORITY

This application claims the priority of U.S. Ser. No. 61/942,709 filed on Feb. 21, 2014, the contents of which are fully incorporated herein by reference.

FIELD OF THE INVENTION

The field of the invention relates to a device and method drawn to transcranial/cranial electrostimulation (TCES/CES) for non-invasive, non-pharmacological treatment for patients experiencing a number of afflictions. Namely providing electrical stimulation through a number of electrodes to alleviate or control symptoms associated with neural imbalances and pain management.

BACKGROUND OF THE INVENTION

Bio-electric stimulation apparatus has been developed for applying current pulses to a patient through electrodes located on opposite sides of the head of the patient. The current pulses at selected frequencies are applied to cause reaction with the central nervous system of the patient. Such devices, referred to as transcranial electrostimulation (TCES) or cranial electrostimulators (CES) have been used for a variety of non-invasive procedures, such as producing analgesic effects, reducing or controlling migraine headaches, and other applications of treatment and electro-anesthesia.

Earliest prototypes of transcranial electrostimulation devices originated in Russia. These original designs, although successfully employed for several different treatment modalities, had a severe drawback with regard to the comfort of the wearer or patient. In some cases, these earlier cranial electrostimulation devices even subjected the wearer to pain. It has been discovered that the reason for the discomfort of these earlier designs was a result of the use of direct current as part of the overall operation of the devices. The direct current was used to break down or lower skin resistance to allow the treatment alternating current signals to penetrate the brain and nervous systems to cause the desired effect established by the placement of the electrodes on the head of the patient.

In these earlier types of machines, the wearer received a combination of direct current and alternating current electrical waveform packages through a series of electrodes affixed to the head with straps. Typically, two electrodes comprising a cathode or negative pole of the DC based circuit would be placed approximately three inches apart to the left and right of the center of the forehead. Two other electrodes, comprising the anode or positive pole of the DC based circuit, were placed on the rear of the skull on the post mandibular area behind and below each ear.

With this DC current based design, the wearer was required to place a thick pad between any electrode and the skin. Typically, the pad was comprised of several layers of unbleached and uncolored cotton flannel, or an equivalent product. For best results, the fabric pads were soaked with water to provide a conductive path between the electrodes and the skin of the wearer. Without the presence of the pads (which were only required because of the presence of the DC current), such devices could either burn the skin of the wearer, or cause relatively intense pain before a usable level of the treatment modality of the currents at the AC frequency could be reached.

Although various types of treatment were employed by such earlier transcranial electrostimulation devices, the devices typically needed to be employed for an average time of thirty minutes per treatment period. Without the presence of the relatively thick cumbersome pads, the DC based design was unusable. With the presence of the thick padding, the DC design was bearable to the wearer, but rarely provided the wearer with a pleasant experience.

Review of Related Technology:

Three Russian patents which utilize such devices for different treatment methods are Russian patents 1489719, 1507404, and 1522500. In all of these patents, a combination of direct current and rectangular impulse current, with a frequency of between 70 and 80 Hertz, was employed at current amperages which were increased from a relatively low level to a higher or maximum level over the course of each treatment session.

An additional and potentially harmful drawback of the DC based designs was that of iontophoresis. A characteristic of a DC circuit application of this type is that molecular sized parts of metal, toxins and other undesirable impurities can be caused to migrate in the direction of current flow through the skin and into the bloodstream of the wearer of such DC based CES devices. Consequently, care had to be taken to ensure that no substance was present other than water used to create good electrical contact with the pad to the skin of the wearer.

Since practically all CES treatment modalities require repeated treatments, the potential for iontophoresis being a harmful factor was escalated. Transcranial electrostimulation (CES or TCES) originally was used in the 1960's to induce sleep. These early devices typically used less than 1.5 mA at 100 Hz. The Liss patent (U.S. Pat. No. 4,627,438) employed higher frequencies modulated by a lower frequency square-wave to produce recurring pulse bursts. The repetition frequency of the device of Liss is determined by the modulation frequency; but the pulse bursts are of uniform amplitude within each repetition cycle.

The device of the Liss patent is specifically directed to utilization in conjunction with the treatment of migraine headaches. The low frequency or modulating signal is asymmetrical, utilizing a 3:1 duty cycle, "on" three-fourths of the time and "off" one fourth of the recurring period. This results in bursts of the high frequency signal separated by the off time when no signal is applied, following the re-application of the bursts of the high frequency signal. Some patient discomfort may be present in such an "on/off" system operation over the period of time of application of the pulse during a treatment interval.

A number of other United States patents, all directed to dual frequency systems which utilize high frequency signals modulated by a low frequency modulation carrier, operating in the general nature of the device of the Liss U.S. Pat. No. 4,627,438, exist. Typical of these patents are the patents to Limoge U.S. Pat. No. 3,835,833; Nawracaj U.S. Pat. No. 4,071,033; Kastrubin U.S. Pat. No. 4,140,133; Morawetz U.S. Pat. No. 4,922,908 and Giordani U.S. Pat. No. 5,131,389. All of these patents employ uniform amplitude high frequency signals, which are modulated at the lower frequency of the modulation carrier.

A variation on the systems of the patents discussed above is disclosed in the Haimovich U.S. Pat. No. 5,540,736. The device of this patent employs two different current generators for providing electrical currents delivered to two electrode pairs operating across different portions of the head of the patient. This allows independent control of the current generators to administer independent regulated electrical current across each of the pairs to adjust for different impedances so caused by the physiological and anatomical differences between different sides of a patient's mid brain portion, the quality of the conducting medium, and other factors. In all other respects, the system disclosed in this patent is similar to the operation of the system disclosed in the Liss patent discussed above.

Russian patent publication No. 2139111 is directed to a method for treating narcomania, which is a treatment also used in others of the CES patents described above for alcohol and narcotic addiction. In this patent, transcranial electrical stimulation is accomplished by means of packets of current with a duration of four milliseconds, at a modulation frequency of 100 Hz. Within each of the packets, the high frequency signals have a uniform frequency and current amplitude.

U.S. Pat. No. 7,769,463 to Katsnelson is directed to a therapeutic electrostimulation apparatus and method that operates to supply electrostimulation signals to three channels. The basic electrostimulation signal for each of the channels is the same; and this signal is applied to a transcranial electrostimulation set of output electrodes. A second channel provided with the same signal is further operated to modulate the signal with a dual frequency signal pattern for the application of the second channel signal to a second set of electrodes, typically applied to the body near the spinal area. A third channel supplied with the basic electrostimulation signal modulates the electrostimulation signal during a portion of a treatment session with a diapason of frequencies varying randomly, and the output of this channel is applied to a set of electrodes at a local area for therapeutic treatment.

U.S. Pat. No. 6,904,322 also to Katsnelson is directed to a transcranial electrostimulation apparatus which employs an asymmetrical signal modulated by a 77.5 Hz modulating signal, with a resultant lowering of the capacitive resistance of the epidermal layer. As a consequence, lower current levels using the Katsnelson system of the '322 patent were found capable of achieving the desired results which previously required much higher current levels. The lower current levels of this system translate into a greater level of comfort for the patient or user of the device of the Katsnelson patent.

There also have been a number of efforts in the past to apply electrical signals to multiple body sites, in an effort to obtain some type of therapeutic result, such as pain relief. Early efforts, such as disclosed in the Phurston U.S. Pat. No. 309,897 and Gavigan U.S. Pat. No. 693,257, applies direct current to pads located at different locations on the body. These devices are subject to the same disadvantages described above for direct current TCES and CES systems, inasmuch as a relatively high level of discomfort or pain may be experienced through the use of direct current applications. Other devices employing stimulation of electrodes applied to the skin or external areas of the body, or implanted in permanent locations for therapeutic purposes, have been devised using alternating current signals. Such devices, however, have not been coordinated or combined with the use of transcranial electrostimulation apparatus, or cranial electro stimulators.

Various devices are known in the art. However, their structure and means of operation are substantially different from the present disclosure. The other inventions fail to solve all the problems taught by the present disclosure. The present invention provides an apparatus and method to reduce and/or eliminate hyperpolarization resulting from long term transcranial electrostimulation of the brain. At least one embodiment of this invention is presented in the drawings below and will be described in more detail herein.

SUMMARY OF THE INVENTION

A transcranial electrostimulation device is described and taught having a source of monopolar pulses of a random frequency, wherein the polarity of the monopolar pulses is constant; a source of bipolar pulses of a random frequency; wherein the polarity of the bipolar pulses reverses after a predetermined time; a source of modulating control signals to yield a frequency less than that produced initially by the monopolar and bipolar pulses; and an amplitude data generating mechanism responsive to the modulating control signals and coupled to the sources of the monopolar and bipolar pulses. The transcranial electrostimulation device may further be capable of inverting the polarity of the bipolar pulses. Further, the transcranial electrostimulation device has a plurality of outputs, wherein the outputs are electrodes attached to a patient for receiving transcranial electrostimulation treatment.

In another aspect of the invention, there is a method of using a transcranial electrostimulation device having the steps of providing a transcranial electrostimulation device comprising, a source of monopolar pulses of a random frequency, wherein the polarity of the monopolar pulses is constant; a source of bipolar pulses of a random frequency; wherein the polarity of the bipolar pulses reverses after a predetermined time; a source of modulating control signals to yield a frequency less than that produced initially by the monopolar and bipolar pulses; and an amplitude data generating mechanism responsive to the modulating control signals and coupled to the sources of the monopolar and bipolar pulses; producing a number of random frequency monopolar tone bursts comprising a number of square wave pulses; repeating the production of the random frequency monopolar tone bursts for a first length of time; producing a number of random frequency bipolar tone bursts comprising a number of square wave pulses; repeating the production of the random frequency bipolar tone bursts for a second length of time, wherein the polarity of the bipolar tone bursts is inverted about every 2 to about every 10 minutes; and delivering the monopolar and bipolar tone burst signals to electrodes of the transcranial electrostimulation device.

Generally, the present invention provides for a device and method that seeks to reduce and/or prevent the occurrence of hyperpolarization of membranes of postsynaptic neurons associated with long term transcranial electrostimulation of the brain. This is caused by the building of inhibitory neurotransmitters from a presynaptic cell to a postsynaptic receptor, which in turn, can make more difficult to generate an action potential through these neurons. Thus, current transcranial stimulation devices and methods can lead to a reduction of the positive effects or a nullification of all positive effects associated with transcranial electrostimulation.

To combat this potential downfall of transcranial electrostimulation, the present invention employs a number of tools including the introduction of a white noise clock generator (random frequency generator) for randomly changing the polarity and wave form of the transcranial electrostimulation. Additionally, results achieved by experimental design show that only saggital direct current can reach the antinociceptive system by passing along a couple intracranial ways, the spinal liquid of basal cisterns and intraventricular. Thus, by using an increased number of targeted positioned electrodes, one can increase the effective results of the transcranial electrostimulation. The end product is a transcranial electrostimulation device that carries an increase in effectiveness and a decrease in the number of contraindication.

In general, the present invention succeeds in conferring the following, and others not mentioned, benefits and objectives.

It is an object of the present invention to provide a transcranial electrostimulation device that provides an increase in effectiveness over existing treatments.

It is an object of the present invention to provide a transcranial electrostimulation utilizes both monopolar and bipolar pulse tones.

It is an object of the present invention to provide a transcranial electrostimulation device that can supply a high amplitude and low amplitude treatment.

It is another object of the present invention to provide a transcranial electrostimulation device that uses precise, targeted electrode placement to elicit an improved patient response.

It is another object of the present invention to provide a transcranial electrostimulation device that utilizes random frequency tone bursts within a prescribed frequency range.

It is another object of the present invention to provide a transcranial electrostimulation device that inverts the polarity of the tone bursts supplied to the patient.

It is yet another object of the present invention to provide a transcranial electrostimulation device that can be used to treat a number of ailments and disease states including pain management, depression, PTSD, Parkinson's disease, and other not mentioned ailments/diseases.

DETAILED DESCRIPTION OF THE DRAWINGS

The preferred embodiments of the present invention will now be described with reference to the drawings. Identical elements in the various figures are identified, as far as possible, with the same reference numerals. Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto without deviating from the innovative concepts of the invention.

Figure 1:
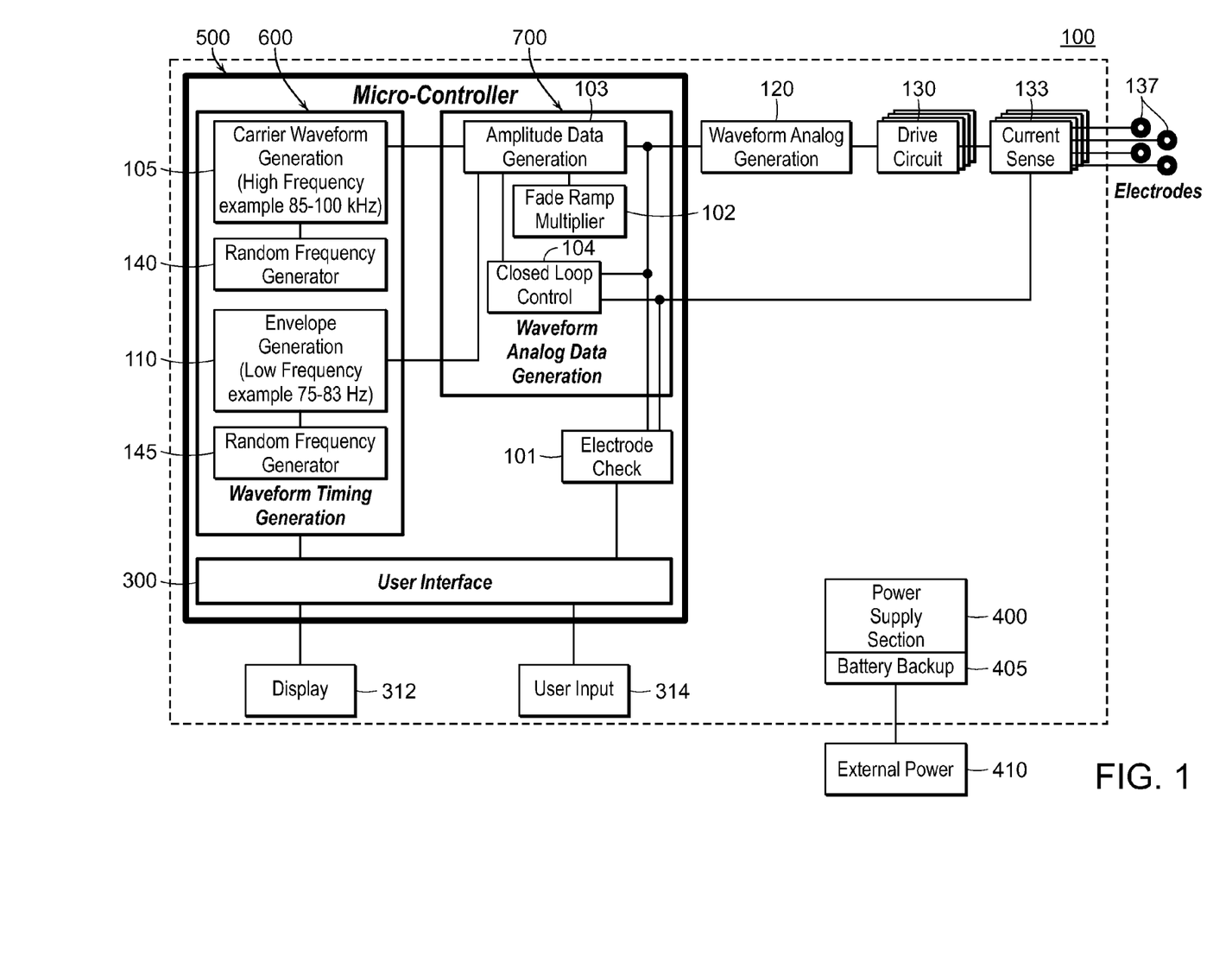
FIG. 1 is a schematic diagram illustrating the principles of operation of a preferred embodiment of the present invention.

Referring now to FIG. 1, there is a schematic diagram showing the present invention that produces waveforms for transcranial electrostimulation applications. The waveform(s) produced and process of using the waveforms provide for a novel apparatus and method of transcranial electrostimulation.

Generally, there is a microcontroller 500 which controls and dictates the general functionality of the device 100. The microcontroller 500 provides the basis for the user interface 300, the waveform timing generation 600, and the waveform analog data generation 700. In the waveform timing generation 600, the transcranial electrostimulation device 100 has a high frequency generator 105 which generates high frequency current signals (i.e. about 65 Hz to about 100 kHz). These high frequency pulses are modulated by a low frequency generator 110 operating in a range from about 70 Hz to about 85 Hz. In some embodiments, there may be a second low frequency generator operating in about 0.001-0.5 Hz and more preferably about 0.002-0.2 Hz.

Each of the high frequency generator 105 and low frequency generator 110 has their own respective random signal generator 140, 145. The random signal generator 140 of the high frequency generator 105 changes the carrier frequency randomly using steps of about 1 to about 10 kHz throughout the treatment process. The random signal generator 145 of the low frequency generator 110 delivers randomly changing frequency impulses using about 0.25 to about 3 Hz steps throughout the treatment process. This produces a "white noise" effect when applied to the waveform for practical treatment purposes.

This "white noise" effect reduces and/or prevents the occurrence of hyperpolarization of membranes of postsynaptic neurons in the brains of individuals receiving transcranial electrostimulation treatment. The high frequency generator 105 and low frequency generator 110 operate over random frequencies within the predefined frequency range(s) as described above. The random frequency changes and polarity inversions of the waveforms created by transcranial electrostimulation device 100 are the driving force behind the limitation or abolishment of hyperpolarization in treatment receiving patients using the present invention.

Further, the aforementioned frequency changes may occur uniform or non-uniform distributions. For example, the low frequency generator 110 has random frequency steps of about 0.25 Hz to about 3 Hz. Thus, the steps may be uniform (0.50 Hz) shifts up or down, or non-uniform (0.45 Hz, 0.80 Hz, 2.2 Hz, etc.) in shifts up or down. This results in greater efficacy of treatment, as well as patient comfort throughout the treatment process. The process and description is similar for the high frequency generator 105.

The transcranial electrostimulation device 100, in generating the waveform analog data 700, receives the random, modulated waveforms generated by the high frequency generator 105 and low frequency generator 110. That information is received by the amplitude generation module 103 which combines the aforementioned data signals into the desired waveform outputs. A fade ramp multiplier module 102 modulates the generated amplitude data 102 to progressively ramp up or down the current injection at the beginning of the treatment, as well as at the transitions of each phase of the treatment.

Additionally, the amplitude generation module 103 will, in some instances, change the polarity of the respective pulse signal each period. The random, modulated, and periodically inverted waveform analog signal is generated 120 by the microcontroller 500. The current sense 133 detects and measures the current of the amplified channel output. The current sense 133 may have analog or digital properties. The drive circuit 130 feeds into the current sense 133. The current sense module 133 can interact with a closed loop control module 104. The closed loop control 104 is based on the signature analysis of the patient in real time. Thus, the voltage can be adjusted to get the desired current output.

In turn, the wave shaping can be accomplished quicker to make the waveforms generated match the patient given the patient response or accumulated patient data. Preferably, there are four outputs 137 having any number of electrodes attached thereto. The difference in resistance between outputs is measured as an internal error signal to help achieve and maintain symmetrization of the current amplitude.

An individual interacts with the transcranial electrostimulation device 100 via a user interface 300. The user interface 300 provides for a display 312 and a user input 314. The display 312 may be an audiovisual display that is capable of displaying data from the microcontroller 500 and outputs 137. The display 312 may further have touch capabilities. The user inputs 314 enable the microcontroller 500 to execute the commands based on the entered parameters. The device is generally powered by an external power source 410 such as a 120V DC power supply. The external power 410 is supplied to the power supply section 400 where the transcranial electrostimulation device 100 uses it to provide electrical energy to the device. In the event of a power outage, or for portability purposes, there is also a battery backup 405 that can power the device for some duration of time.

The transcranial electrostimulation device 100 further may have an electrode check 101. The current sense module 133 has a return path which measures the impedance present in each of the respective outputs 137. This return path is an integral part of the closed loop control module 104, but also serves as an electrode check 101. If any of the aforementioned pathways directed to a particular output 137 does not match the expected human impedance, such as if an electrode becomes disrupted or detached from the patient, then the transcranial electrostimulation device 100 will issue a warning through the user interface 300 alerting the physician or device operator.

Figure 2:
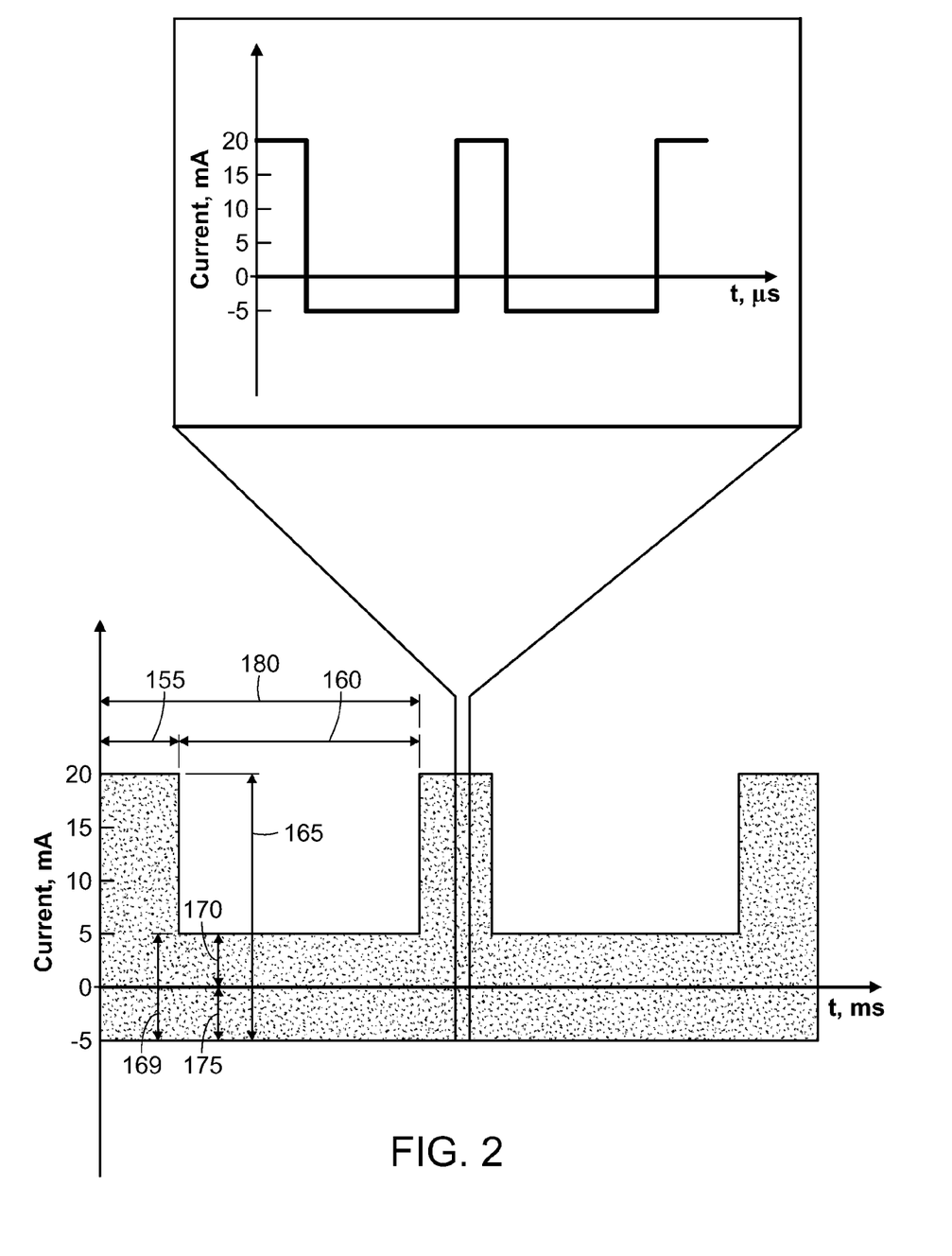
FIG. 2 is a graphical representation of the monopolar modulation stage of transcranial electrostimulation consistent with the present invention.
Figure 3A:
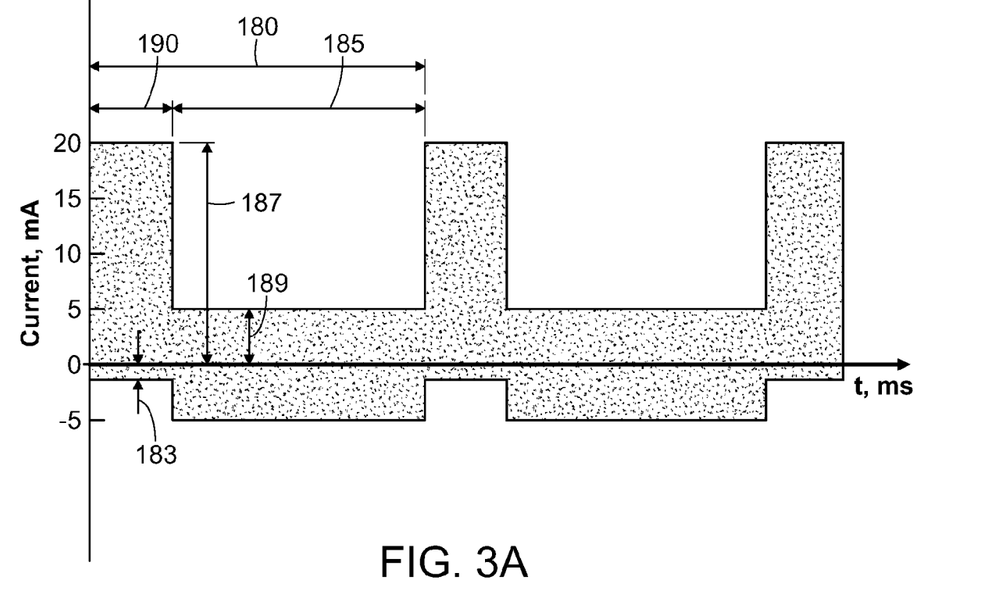
FIG. 3A is a graphical representation of the positive polar pulses of the bipolar modulation stage of transcranial electrostimulation consistent with the present invention.
Figure 3B:
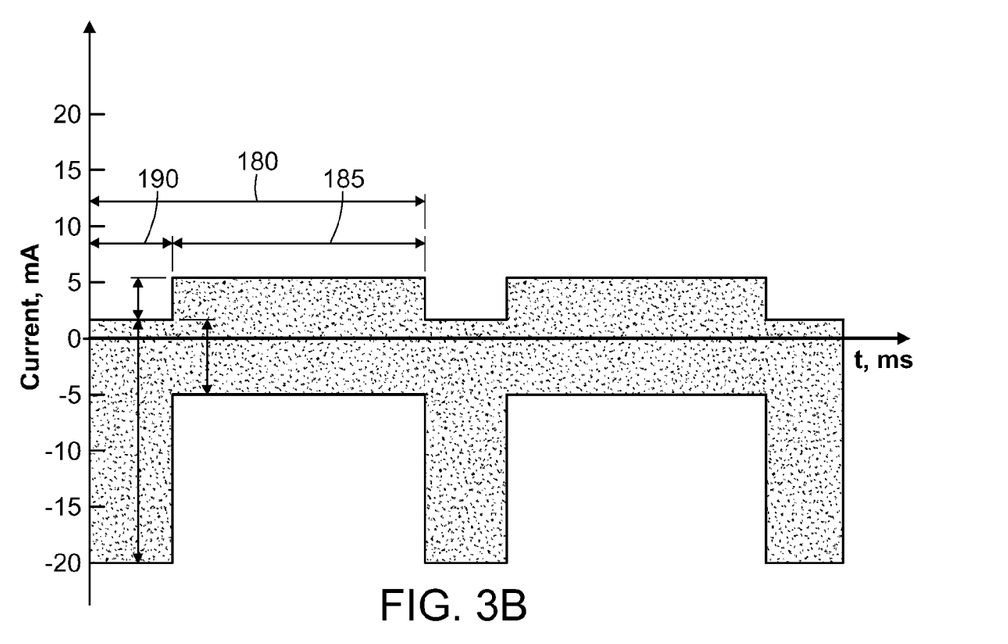
FIG. 3B is a graphical representation of the negative polar pulses of the bipolar modulation stage of transcranial electrostimulation consistent with the present invention.

The operation of the device 100 as described in FIG. 1 produces the waveforms present in FIGS. 2-3B. In FIG. 2, there is a graphical representation of the monopolar modulation tone burst. The graphical representation is charted as values of current versus time. The modulation frequency is varied randomly with uniform distribution over the time interval over about 75 to about 83 Hz with a frequency step of about 0.25 Hz and a time step of approximately 5 seconds. The monopolar modulation has pulses alternating between a high amplitude pulse 165 and a lower amplitude pulse 169 which is controlled by the microcontroller 500. One cycle of the high amplitude pulse 165 and low amplitude pulse 169 forms a pulse period 180. The pulse period 180 can range from about 0.1 seconds to about 10 minutes. The high amplitude pulse 165 comprises approximately 25% of the pulse period 180 or a first time duration 155. The remaining portion of the pulse period 180 comprises the low amplitude pulse 169 or a second time duration 160. Additionally, there should be a ratio of about 1:4 for the current of the low amplitude pulse 169 and the high amplitude pulse 165. These ratios create a constant, yet random frequency, square waveform for the duration of the monopolar modulation portion of the treatment cycle. The enlarged portion of the waveform shows the minute variance that comprises the general square waveform structure.

FIGS. 3A and 3B show the second portion of the treatment cycle comprising a two stage bipolar modulation waveform. In FIG. 3A, there is a graphical representation of the positive modulation pulses, whereas FIG. 3B illustrates the second stage negative modulation pulses. The positive modulation phase comprises a similarly shaped waveform compared to the monopolar modulation. The waveform comprises a positive high amplitude pulse 187 and a positive low amplitude pulse 189. The ratio between the positive high amplitude pulse 187 and the positive low amplitude pulse 189 is 4:1.

There is a slight negative characteristic to the positive high amplitude pulse 187, which is more pronounced during the positive low amplitude pulse 189. The pulse period 180 is represented by the pulse period of the high amplitude phase 190 and the pulse period of the low amplitude phase 185. The exact time of each respective period 185, 190 may vary, but it is preferable that the high amplitude period 190 is about three times shorter than the low amplitude period 185. However, the negative portion of the positive modulation pulse is less than that of the monopolar modulation pulse. This waveform is repeated throughout the positive modulation pulse phase.

In turn, the negative modulation pulse substantially minors that of the positive modulation pulse. The high amplitude period 190 and low amplitude period 185 form the total pulse period 180. The bipolar modulation pulses have their polarities reversed approximately every about 5 to about 10 minutes during the bipolar modulation phase of the treatment. Overall, between the two phases (monopolar and bipolar) the microcontroller 500 and the drive circuit 130 can be used to change the current applied by the device 100 while maintaining the above described waveform. The microcontroller 500 measures the magnitude of the current supplied by the system. The microcontroller 500 may be capable of displaying and/or recording the maximum and minimum amplitude of the waveform.

Figure 4:
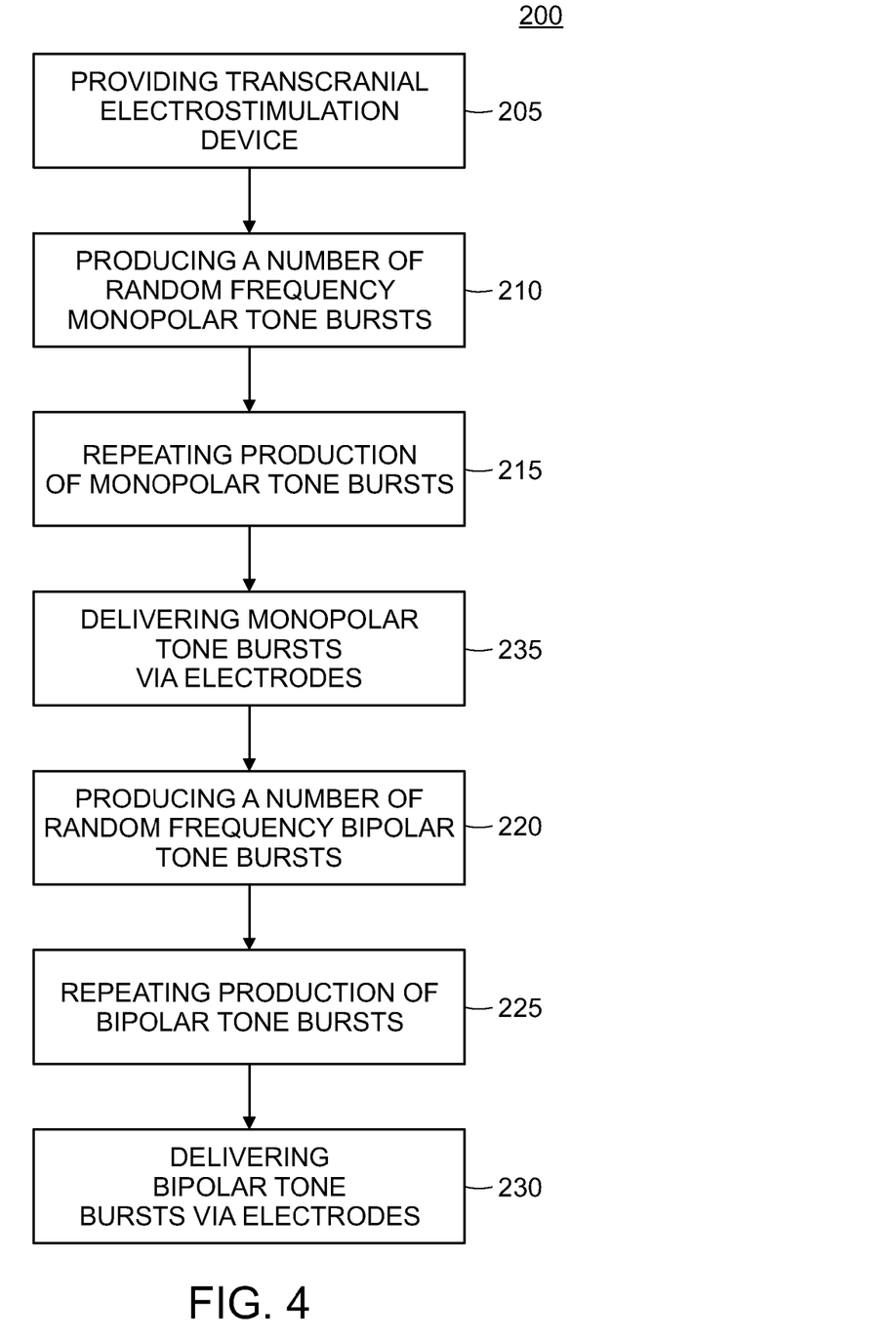
FIG. 4 is a flow chart illustrating a method of use of the present invention.

FIG. 4 outlines the present methodology associated with the transcranial electrostimulation device 100. The method 200, in box 205, first involves providing a transcranial electrostimulation device as described in FIG. 1. Here, the electrode outputs 137 (see FIG. 1) are placed on a patient. There is an electrode with zero potential (cathode) placed on the forehead or comparable area, and another electrode (anode) placed on the neck area. Two additional symmetric electrodes (anodes) are placed in symmetric locations behind the ears.

The transcranial electrostimulation device is then used, in box 210, to produce a number of random frequency monopolar tone bursts as previously described. In addition, the production of the monopolar tone bursts begins with a ramping up of the current injection. This ramping up (or down) occurs at the beginning of treatment, at transitions between each phase of the treatment, and at the end of the treatment. The phase transitions include monopolar tone bursts, bipolar positive amplitude tone bursts, and bipolar negative amplitude tone bursts. This ramping up or down of the current injection occurs over about 2 to about 15 seconds and more preferably about 5 seconds. This gradual increase/decrease of current provides a distinct advantage over other similarly situated devices as described above.

In box 215, the monopolar tone bursts are repeated for a duration of time. Empirical evidence suggests that the ideal frequency is about 77.5 Hz, but a frequency in the ranges of about 70 Hz to about 85 Hz and more preferably about 75 Hz to about 83 Hz are effective as well. In a box 235, these monopolar tone bursts are applied to the patient for approximately 10-25 minutes and more preferably approximately 15-20 minutes. The polarity of the tone bursts remains constant (positive) throughout the duration of this phase of the treatment.

In box 220, the treatment shifts to producing a number of random frequency bipolar tone bursts.

These bipolar tone bursts are repeated, as shown in box 225, for a second duration of time of approximately 15-30 minutes and more preferably approximately 20-25 minutes. The bipolar tone bursts carry a similar inverse frequency as the positive modulated bipolar tone bursts described above. Additionally, the bipolar tone bursts have their polarity reversed approximately every 5 to about every 10 minutes.

Thus, a patient would be subjected to about 5 minutes of positive modulated pulses, and then 5 minutes of negative modulated pulses or about 10 minutes of positive modulated pulses and then about 10 minutes of negative modulated pulses.

These tone bursts are delivered to the patient via electrodes adhered to the patient as shown in box 230. Upon completion of the treatment, which lasts about 30-55 minutes and more preferably about 40-45 minutes, the electrodes are removed. In general, for low amplitude treatments, the current for the monopolar and bipolar modulation are substantially similar. For high amplitude treatments, the current for the monopolar modulation is approximately one-third to one-half of the current of the bipolar modulation current.

Generally, the transcranial electrostimulation device 100 provides an improvement to current treatments employing such methodologies. A side effect of long term transcranial electrostimulation can result in hyperpolarization in the membrane of the post synaptic neurons. This electrical charge can make it difficult for the neuron to then generate an action potential, which can prevent the release of various neuropeptides. This, in turn, can limit or reduce the positive effects of transcranial stimulation.

The current transcranial electrostimulation device 100 uses white noise (clock) generators 105, 110. The inclusion of such elements randomly changes some of the parameters of the waveform and can lead to a reversal of polarity for some of the modulated pulses. Further, the present transcranial electrostimulation device 100 employs four rather than three electrodes. Evidence has shown that by inclusion of an additional electrode and the particular placement of the electrodes described above will increase the number of deep brain structures activated by the transcranial electrostimulation treatment.

What is claimed is:

1. A transcranial electrostimulation device comprising:
    a first generator configured to produce alternating current electric pulses of a random frequency,
        wherein a polarity of the alternating current electric pulses is constant;
    a second generator configured to produce both alternating and direct current electric pulses of a random frequency;
        wherein the alternating and direct current electric pulses of the second generator modulates the alternating direct current electric pulses produced by the first generator forming modulated control signals;
    an inverter coupled to the first generator and the second generator,
        wherein the inverter is configured to reverse the polarity of the alternating and/or direct current electric pulses generated by each generator;
    an amplitude data generating mechanism responsive to the modulated control signals and coupled to the first and the second generator; and
    four electrodes configured to be coupled to a skin surface of a patient and deliver the modulated control signals to the patient.

2. The transcranial electrostimulation device of claim 1 wherein the frequency of the pulses produced by the first generator is about 85 kHz to about 100 kHz and the frequency of the pulses produced by the second generator is about 60 Hz to about 90 Hz.

3. The transcranial electrostimulation device of claim 1 further comprising a current sense module,
    wherein the current sense module is configured to measure a resistance between at least two of the four electrodes.

4. The transcranial electrostimulation device of claim 3 wherein the resistance measurements are used to create symmetry between the current amplitudes of the four electrodes.

5. The transcranial electrostimulation device of claim 2 wherein the frequency of the pulses produced by the first generator are configured to randomly change in increments of about 1 kHz to about 10 kHz and the frequency of the pulses produced by the second generator are configured to randomly change in increments of about 0.2 Hz to about 0.3 Hz.

6. A method of providing transcranial electrostimulation comprising the steps of:
    providing a transcranial electrostimulation device;
    producing a number of first random frequency bipolar pulses comprising a number of square wave pulses,
        wherein the first random frequency bipolar pulses are modulated by a number of second random frequency pulses of a constant polarity forming modulated pulses;
    delivering, to a patient, the modulated pulses for a first length of time,
        wherein during the first length of time the modulated pulses are of a constant polarity;
    continuing to produce and deliver the modulated pulses for a second length of time,
        wherein during the second length of time the polarity of the modulated pulses is inverted every about 2 minutes to about 10 minutes during the second length of time; and
    wherein the modulated pulses are delivered via four electrodes of the transcranial electrostimulation device,
        wherein the four electrodes are coupled to a skin surface of a patient.

7. The method of claim 6 wherein approximately one-third to one-half of the total treatment time will subject the patient to the modulated pulses with a monopolar waveform.

8. The method of claim 7 wherein the remaining treatment time will subject the patient to the modulated pulses with a bipolar waveform.

9. The method of claim 6 wherein there is a progressive ramp up or down of the current injection at the beginning of treatment, at each phase shift, and at the end of the treatment.

10. The method of claim 6 wherein an overall waveform produced by the first random frequency pulses and the second random frequency pulses has both positive and negative amplitude characteristics.

11. The method of claim 10 wherein the second random frequency pulses have an overall positive waveform.

12. The method of claim 10 wherein the second random frequency pulses have an overall negative waveform.

13. The method of claim 11 wherein a difference between a positive high amplitude peak and a positive low amplitude peak is present in a 4:1 ratio.

14. The method of claim 11 wherein a difference between a negative high amplitude peak and a negative low amplitude peak is present in a 4:1 ratio.

15. The method of claim 12 wherein a difference between a positive high amplitude peak and a positive low amplitude peak is present in a 4:1 ratio.

16. The method of claim 12 wherein a difference between a negative high amplitude peak and a negative low amplitude peak is present in a 4:1 ratio.

17. The method of claim 11 wherein during a pulse period a high amplitude phase is about three times shorter than the low amplitude phase.

18. The method of claim 11 wherein during a pulse period a high amplitude phase is about three times shorter than the low amplitude phase.

19. The method of claim 6 wherein an area of a positive waveform region of the bipolar pulses is equal to an area of the negative waveform region of the bipolar pulses.

\* \* \* \* \*